United States Patent
Saunders et al.

(10) Patent No.: US 11,771,765 B2
(45) Date of Patent: Oct. 3, 2023

(54) LIGHT AUGMENTED TREATMENT METHOD

(71) Applicant: The Procter & Gamble Company, Cincinnati, OH (US)

(72) Inventors: Charles Winston Saunders, Fairfield, OH (US); Robert Scott Youngquist, Mason, OH (US); Lijuan Li, Lebanon, OH (US); Justin Angelo Caserta, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 123 days.

(21) Appl. No.: 16/913,191

(22) Filed: Jun. 26, 2020

(65) Prior Publication Data

US 2020/0405859 A1    Dec. 31, 2020

Related U.S. Application Data

(60) Provisional application No. 62/868,179, filed on Jun. 28, 2019.

(51) Int. Cl.
| | |
|---|---|
| *A61K 41/00* | (2020.01) |
| *A61K 31/44* | (2006.01) |
| *A61K 31/4412* | (2006.01) |
| *A61K 31/444* | (2006.01) |

(52) U.S. Cl.
CPC .......... *A61K 41/0057* (2013.01); *A61K 31/44* (2013.01); *A61K 31/444* (2013.01); *A61K 31/4412* (2013.01)

(58) Field of Classification Search
CPC ................ A61K 8/4933; A61K 8/4926; A61K 2800/81; A61K 41/0057; A61K 31/444; A61K 31/44; A61K 31/4412; A61Q 5/006
See application file for complete search history.

(56) References Cited

U.S. PATENT DOCUMENTS

| | | |
|---|---|---|
| 434,080 A | 8/1890 | Faulkner |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,658,072 A | 11/1953 | Milton |
| 2,666,058 A | 1/1954 | Neher |
| 2,809,971 A | 10/1957 | Bernstein et al. |
| 3,236,733 A | 2/1966 | Karsten et al. |
| 3,332,880 A | 7/1967 | Adriaan et al. |
| 3,753,196 A | 8/1973 | Kurtz et al. |
| 3,761,418 A | 9/1973 | Parran |
| 3,929,678 A | 12/1975 | Laughlin |
| 4,323,683 A | 4/1982 | Bolich, Jr. et al. |
| 4,345,080 A | 8/1982 | Bolich, Jr. |
| 4,379,753 A | 4/1983 | Bolich, Jr. |
| 4,470,982 A | 9/1984 | Winkler |
| 4,835,149 A | 5/1989 | Burke et al. |
| 5,753,600 A | 5/1998 | Kamegai et al. |
| 5,886,031 A | 3/1999 | Shin et al. |
| 5,968,539 A | 10/1999 | Beerse et al. |
| 6,017,936 A | 1/2000 | Polson et al. |
| 6,165,484 A | 12/2000 | Raad et al. |
| 6,426,093 B1 | 7/2002 | Chevion et al. |
| 6,495,089 B1 | 12/2002 | Crider |
| 6,846,777 B2 | 1/2005 | Antoni-zimmermann et al. |
| 8,119,168 B2 | 2/2012 | Johnson et al. |
| 8,372,440 B2 | 2/2013 | Jeanjean et al. |
| 8,506,942 B2 | 8/2013 | Burry et al. |
| 8,933,193 B2 | 1/2015 | O'sullivan et al. |
| 8,980,876 B2 | 3/2015 | Schwartz et al. |
| 9,381,148 B2 | 7/2016 | Schwartz et al. |
| 2003/0199490 A1 | 10/2003 | Antoni-zimmermann et al. |
| 2004/0058855 A1 | 3/2004 | Schwartz et al. |
| 2005/0202984 A1 | 9/2005 | Schwartz et al. |

(Continued)

FOREIGN PATENT DOCUMENTS

| | | |
|---|---|---|
| CN | 1324825 A | 12/2001 |
| CN | 1325892 A | 12/2001 |

(Continued)

OTHER PUBLICATIONS

J. Biochem., 1976,vol. 80, No. 4,p. 799-804URL,https://www.jstage.jst go.jp/article/biochemistry1922/80/4/80_4_799/_pdf.
"Biochemistry" JIN Fengxie China Light Industry Press dated Aug. 31, 2004, p. 346-351.
"Manual of Rational use of Anti-microorganism agents" Jsong Jinchun, etal. Science Press, dated Jan. 31, 2009, p. 409-410.
15590 PCT Search Report and Written Opinion for PCT/US2020/039495 dated Jun. 10, 2020.
All Office Actions, U.S. Appl. No. 13/283,890, filed Oct. 28, 2011.
All Office Actions, U.S. Appl. No. 13/283,894, filed Oct. 28, 2011.
Andrew J. Wiemer et al., "A live imaging cell motility screen identifies prostaglandin E 2 as a T cell stop signal antagonist", The Journal of Immunology, vol. 187, No. 7, Oct. 1, 2011, 9 pgs.
Anonymous: "Mixtures of fungicides and insecticides", Research disclosure, Kenneth Mason Publications, Hampshire UK, GB, vol. 338, No. 93, Jun. 1, 1992, 9 pgs.
Bharadwaj, et al. "Invitro Study to Evaluate the Synergisitc Activity of Norfloxacin and Metronidazole" Indian J Pharmacol 2003, 35: 220-226.

(Continued)

*Primary Examiner* — Jianfeng Song
(74) *Attorney, Agent, or Firm* — Linda M. Sivik

(57) ABSTRACT

The present invention is directed to a method of treating skin and scalp comprising applying on the scalp or skin a composition comprising a scalp care active selected from the group consisting of 2-Pyridinol-N-oxide, a pyrithione or a polyvalent metal salt of pyrithione, one or more iron chelator having an A log P value of greater than or equal to 0.4 and mixtures therein; exposing the scalp and skin to electromagnetic radiation having wavelength from about 350 nm to about 500 nm and power from about about 0.1 mWatts/cm$^2$ to about 1000 mWatts/cm$^2$ and for a time period from about 2 seconds to about 5 minutes; wherein the antimicrobial treatment results in reduction of fungal growth as measured by the Fungal Growth Sensitivity Test of at least 50% compared to the dark sample.

7 Claims, No Drawings

(56) References Cited

U.S. PATENT DOCUMENTS

| | | | |
|---|---|---|---|
| 2006/0013796 | A1 | 1/2006 | Chandra |
| 2006/0089342 | A1 | 4/2006 | Gavin et al. |
| 2006/0167531 | A1* | 7/2006 | Gertner ............... A61N 5/0603 607/86 |
| 2006/0211056 | A1 | 9/2006 | Dellagi et al. |
| 2007/0243222 | A1 | 10/2007 | Lawyer et al. |
| 2009/0298805 | A1 | 12/2009 | Polson et al. |
| 2010/0129434 | A1 | 5/2010 | Ibrahim et al. |
| 2010/0173833 | A1 | 7/2010 | Lajoie et al. |
| 2010/0286037 | A1 | 11/2010 | Dal et al. |
| 2011/0037002 | A1* | 2/2011 | Johnson ............... A61N 5/0613 250/493.1 |
| 2012/0071519 | A1 | 3/2012 | Capodanno et al. |
| 2012/0207688 | A1 | 8/2012 | Guthery |
| 2013/0108610 | A1 | 5/2013 | Schwartz et al. |
| 2013/0109664 | A1 | 5/2013 | Schwartz et al. |
| 2015/0238774 | A1* | 8/2015 | Anderson ............. A61K 35/04 604/20 |
| 2016/0008295 | A1* | 1/2016 | Tseng ...................... A61P 17/00 424/443 |
| 2016/0310393 | A1 | 10/2016 | Chang |
| 2017/0225006 | A1* | 8/2017 | Anderson ................ A61K 9/06 |
| 2018/0221318 | A1 | 8/2018 | Bianchini et al. |
| 2019/0142002 | A1* | 5/2019 | Premachandran ..... A01N 43/36 424/405 |

FOREIGN PATENT DOCUMENTS

| | | | |
|---|---|---|---|
| CN | 103347524 | A | 10/2013 |
| CN | 106573155 | A | 4/2017 |
| EP | 0158481 | A2 | 10/1985 |
| EP | 0800814 | A2 | 10/1997 |
| FR | 2938766 | A1 | 5/2010 |
| JP | H1036233 | A | 2/1998 |
| JP | 2001265018 | A | 9/2001 |
| JP | 2002363077 | A | 12/2002 |
| JP | 2006045126 | A | 2/2006 |
| JP | 2006045127 | A | 2/2006 |
| JP | 2007223917 | A | 9/2007 |
| JP | 2008542259 | A | 11/2008 |
| KR | 20110120569 | A | 11/2011 |
| KR | 1020120018739 | A | 3/2012 |
| WO | 0100151 | A1 | 1/2001 |
| WO | 0153495 | A1 | 7/2001 |
| WO | 0172815 | A1 | 10/2001 |
| WO | 2008046569 | A1 | 4/2008 |
| WO | 2008145848 | A2 | 12/2008 |
| WO | 2009098230 | A2 | 8/2009 |
| WO | 2012058557 | A2 | 5/2012 |
| WO | 2018112106 | A1 | 6/2018 |

OTHER PUBLICATIONS

Bohn M, Kraemer KT. Dermatopharmacology of ciclopirox nail lacquer topical solution 8% in the treatment of onychomycosis. JAm Acad Dermatol. Oct. 2000;43(4 Suppl):S57-69.
Burow, Luke C. "Anaerobic central metabolic pathways active duringpolyhydroxyalkanoate production in uncultured cluster 1 Defluviicoccus enrichedinactivated sludge communities" FEMS Microbiology Letters, Sep. 2009,vol. 298(1), p. 79-84.
Dadak V. "Electron transfer in Paracoccus denitrificans with the modified fbc operon" Folia Microbial (Praha). Nov. 2009;54(6):475-82. Epub Feb. 7, 2010.
Duan,X. "Reactivity of nitric oxide with the [ 4Fe—4S] cluster of dihydroxyaciddehydratase from Escherichia coli" Biochem. J. 2009, 417, p. 783-789.
Fang J., "Rotenone-insensitive NADH dehydrogenase is a potential source ofsuperoxide in procyclic Trypanosoma brucei mitochondria" Mol Biochem Parasitol.Aug. 28, 2002; 123(2): 135-42.
Fisher J. "Anthracycline antibiotic reduction by spinach ferredoxin-NADP+ reductaseand ferredoxin." Biochemistry. Jul. 2, 1985;24(14):3562-71.
Geib N, "Genome mining in Amycolatopsis balhimycina for ferredoxins capable ofsupporting cytochrome P450 enzymes involved in glycopeptide antibiotic biosynthesis" FEMS Microbial Lett. May 2010;306(1):45-53. Epub Feb. 22, 2010.
Gutierrez-Cirlos EB, "Inhibitory analogs of ubiquinol act anti-cooperatively on the Yeast cytochrome bc 1 complex. Evidence for an alternating, half-of-the-sitesmechanism of ubiquinol oxidation" J Biol Chem. Jan. 11, 2002;277(2):1195-202. EpubNov. 7, 2001.
Haraguchi H. "Mode of antibacterial action of totarol, a diterpene from Podocarpusnagi" Planta Med. Apr. 1996;62(2):122-5.
Hughes LM. "Probing binding determinants in center P of the cytochrome bc(I)complex using novel hydroxy-naphthoquinones" Biochim Biophys Acta. Jan. 2010; 1797(1):38-43. Epub Aug. 4, 2009.
Hyde, G. et al. Cosmetic and Drug Preservation "Sodium and Zinc Omadine" 1984, Dekker, D New York; pp. 115-121and124-128.
Hyun Seung Wi et al., "The anti-fungal effect of light emitting diode on yeasts", Journal of Dermatological Science, vol. 67, No. 1, Apr. 4, 2012, pp. 3-8.
Ibrahim, A.S. et al. "Deferiprone iron chelation as a novel therapy for experimental mucormycosis" Journal of Antimicrobial Chemotherapy (2006), 58(5); 4 pages.
Kang Y.S. "Overexpressing antioxidant enzymes enhances naphthalene biodegradationin Pseudomonas sp. strain Asl" Microbiology. Oct. 2007;l53(Pt 10):3246-54.
Ke-Hung Tsui. "Zinc blocks gene expression of mitochondrial aconitase in humanprostatic carcinoma cells" International Journal of Cancer, vol. 118, Issue 3, pp. 609-615, Feb. 1, 2006.
Kessl JJ., "Parameters determining the relative efficacy of hydroxy-naphthoquinoneinhibitors of the cytochrome bc 1 complex" Biochim Biophys Acta. Apr. 2007;1767(4):319-26. Epub Feb. 27, 2007.
Kuipers, M.E. "Synergistic Fungistatic Effects of Lactoferrin in Combination with Antifungal Drugs against Clinical Candida Isolates" Antimicrobial Agents and Chemotherapy (1999), 43(11), 2635-2641.
Lemesre JL, "Leishmania spp.: nitric oxide-mediated metabolic inhibition ofpromastigote and axenically grown amastigote forms" Exp Parasitol. May 1997;86(1 ):58-68.
Mabicka, A., et al. "Synergistic wood preservations involving EDTA, Irganox 1076 and D 2-hydroxypyridine-N-oxide" International Biodelerioration & Biodegredalion 55 (2005) 203-211.
Morita, H "Reactivity of nitric oxide with the [ 4Fe—4S] cluster of dihydroxyaciddehydratase from Escherichia coli" Bioscience Biotechnology and Biochemistry, May 2004, vol. 68(5), p. 1027-34.
Nakayama Y., "Inhibitor studies of a new antibiotic, korormicin, 2-n-heptyl-4-hydroxyquinoline N-oxide and Ag+ toward the Na+-translocating NADH-quinonereductase from the marine Vibrio alginolyticus" Biol Pharm Bull. Oct. 1999;22(10):1064-7.
Nyilasi, Ildiko, et al. "Iron gathering of opportunistic pathogenic fungi"; Acta Microbiologica et Immunologica Hungarica (2005), 52(2), 185-197.
Pierard-Franchimont C., et al., "Revisiting dandruff", International Journal of Cosmetic Science, Kluwer Academic Publishers, Dordrecht, NL, vol. 28, No. 5, Oct. 1, 2006, pp. 311-318.
Pippard MJ, Jackson MJ, Hoffman K, Petrou M, Modell CB. Iron chelation using subcutaneous infusions of diethylene triaminepenta-acetic acid (DTPA). Scand J Haematol. May 1986;36(5):466-72.
Tapia L.,"Effect of 13-epi-sclareol on the bacterial respiratory chain" Planta Med.Nov. 2004;70(11):1058-63.
Zarember, KA, et al. "Antifungal activities of natural and synthetic iron chelators alone and in combination with azole and polyene antibiotics against Aspergillus fumigatus"; Antimicrobial Agents and Chemotherapy (2009), 53(6), 2654-2656.
Ziqiang Yu, "Zinc inhibits mitochondrial aconitase expression in prostate cancer cells" Cellular and Molecular Biology 4: Gene Expression I, Proc Amer Assoc Cancer Res,vol. 4 7, 2006.
"Erythrulose-Self Tanning—Cosmetic & Personal Care", M.C. Biotec Inc., https:www.mcbiotec.com/products/?type=detail&id= 10; dated Sep. 17, 2013, 2 pages.
Lushchak, O.V. et al., "Sodium Nitroprusside Induces Mild Oxidative Stress in Saccharomyces cerevisiae" REDOX Report, vol. 13, No. 4, accepted on Feb. 29, 2008, pp. 144-152.

(56) References Cited

OTHER PUBLICATIONS

Qizhuang et al., "Studies on the spectra and antibacterial properties of rare earth dinuclearcomplexes with L-phenylalanine and 0-phenanthroline", Materials Letters, vol. 60, No. 3, Available online Sep. 21, 2005, pp. 317-320.

Takashi Suzuki, et al., "The Aconitase of Yeast IV. Studies on Iron and Sulfur in Yeast Aconitase", Journal of biochemistry, vol. 80, No. 4, published on Mar. 2, 1976, p. 799-804.

\* cited by examiner

LIGHT AUGMENTED TREATMENT METHOD

FIELD OF THE INVENTION

The present invention relates to a method of treating scalp or skin using a composition comprising an effective amount of an anti-microbial active, such as a metal salt of pyrithione or piroctone olamine and a chelating agent combined with exposure of the part of the scalp or the skin to which the composition is applied to electromagnetic radiation that corresponds to UV-Visible spectrum at wavelength of 350 nm to 500 nm, More particularly, the method of treatment of the present invention relates to the treatment of microbial and fungal infections on the skin or scalp. Even more particularly, the present invention relates to methods for the treatment of dandruff and they provide improved anti-dandruff activity.

BACKGROUND OF THE INVENTION

Various antimicrobial composition, including anti-dandruff compositions, and methods are commercially available or otherwise known in the shampoo art. These methods use compositions that typically comprise particulate, crystalline anti-microbial agents dispersed and suspended throughout the composition or surfactant-soluble anti-microbial agents that are soluble in the product. During the application of the product on the skin or scalp, the antimicrobial actives are deposited on the skin or scalp. Despite the options available, consumers still desire hair and skin methods and products that provides superior anti-microbial efficacy, and further anti-dandruff efficacy versus currently marketed method and products; as such consumers have found that dandruff is still prevalent and superior efficacy can be difficult to achieve.

The present invention has surprisingly found that application on the scalp or skin of compositions that comprise an antimicrobial active, which may include an anti-fungal active or an anti-dandruff active, and a chelating agent followed by exposure of the skin or scalp with electromagnetic radiation that corresponds to UV-Visible spectrum at wavelength of 350 nm to 500 nm provides superior efficacy compared to the efficacy achieved by a method of treatment that does not include such an exposure of electromagnetic radiation.

SUMMARY OF THE INVENTION

The present invention is directed to a method of treating skin and scalp comprising applying on the scalp or skin a composition comprising a scalp care active selected from the group consisting of 2-Pyridinol-N-oxide, a pyrithione or a polyvalent metal salt of pyrithione, one or more iron chelator having an A log P value of greater than or equal to 0.4 and mixtures therein; exposing the scalp and skin to electromagnetic radiation having wavelength from about 350 nm to about 500 nm and power from about 0.1 mWatts/cm$^2$ to about 1000 mWatts/cm$^2$ and for a time period from about 2 seconds to about 5 minutes; wherein the antimicrobial treatment results in reduction of fungal growth as measured by the Fungal Growth Sensitivity Test of at least 50% compared to the dark sample.

DETAILED DESCRIPTION OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Where amount ranges are given, these are to be understood as being the total amount of said ingredient in the composition, or where more than one species fall within the scope of the ingredient definition, the total amount of all ingredients fitting that definition, in the composition.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Scalp Care Actives a) Pyrithione or a Polyvalent Metal Salt of Pyrithione

In an embodiment, the present may comprise pyrithione or a polyvalent metal salt of pyrithione. Any form of polyvalent metal pyrithione salts may be used, including platelet and needle structures. In an embodiment, salts for use herein include those formed from the polyvalent metals magnesium, barium, bismuth, strontium, copper, zinc, cadmium, zirconium and mixtures thereof, and in a further embodiment, zinc. In a further embodiment, for use herein is the zinc salt of 1-hydroxy-2-pyridinethione (known as "zinc pyrithione" or "ZPT"); in yet a further embodiment, ZPT in platelet particle form, wherein the particles have an average size of up to about 20 μm, and in an embodiment have an average size of up to about 5 μm, and yet in a further embodiment have an average size of up to about 2.5 μm.

Pyridinethione anti-microbial and anti-dandruff agents are described, for example, in U.S. Pat. Nos. 2,809,971; 3,236,733; 3,753,196; 3,761,418; 4,345,080; 4,323,683; 4,379,753; and 4,470,982.

It is further contemplated that when ZPT is used as the anti-microbial particulate in the anti-microbial compositions herein, that an additional benefit of hair growth or re-growth may be stimulated or regulated, or both, or that hair loss may be reduced or inhibited, or that hair may appear thicker or fuller.

Zinc pyrithione may be made by reacting 1-hydroxy-2-pyridinethione (i.e., pyrithione acid) or a soluble salt thereof with a zinc salt (e.g. zinc sulfate) to form a zinc pyrithione precipitate, as illustrated in U.S. Pat. No. 2,809,971.

Embodiments include from about 0.01% to about 5% of a pyrithione or polyvalent metal salt of a pyrithione; and from about 0.01% to about 5% of an iron chelator; more in an embodiment, each from about 0.1% to about 2%.

In embodiments having a pyrithione or polyvalent metal salt of pyrithione, the ratio of iron chelator to pyrithione or a polyvalent metal salt of pyrithione may be in the range of 1:10 to 10:1.

b) Iron Chelators

In the present invention, iron chelators may have, but not be limited to, the following characteristics:
1. An affinity for iron ions in either the ferrous (iron II) or ferric (III) forms;
2. Materials of Description 1 (above) that have a denticity of two or higher (denticity is the number of groups of a molecule that bind to the iron ion);
3. Chemical descriptions that are a subset of Description 2:
   a. Either natural or synthetic (e.g., DFO, DFT) materials;
   b. Materials of the following chemical classes:
      i. Catechols and phenols
      ii. Hydroxamates (desferrioxamine (DFO))
      iii. Thiohydroxamates
      iv. Hydroxypyridones (CP20, piroctone, ciclopirox, HP-101)
      v. Hydroxythiopyridones
      vi. Hydroxypyridinethiones
      vii Aminocarboxylates (EDTA, DTPA)
      viii Pyridines (2,2'-bipyridine, 1,10-phenatholine, TPEN)
      ix. Hydroxycarboxylates
      x. Aroylhydrazones (PIH)
      xi. Hydroxyquinolines (8-hydroxyquinoline)
      xii. Hydroxypyrones (maltol, ethyl maltol)
      xiii. Hydroxythiopyrones
      and molecules representing combinations of these chemical classes.

N-Hydroxy-6-octyloxypyridine-2(1H)one, ethanolamine salt, (HP-101) as supplied from Arch Chemicals, Inc., is part of the N-Hydroxypyridones. The N-Hydroxypyridones have alkyl ether substitutions at the 6-position as free acids, ethanolamine salts and metal salts such as zinc, N-Hydroxy-6-octyloxypyridine-2(1H)one, zinc salt. The alkyl ether substituent is from 2-22 carbons in length, either linear or branched.

For the zinc salts of materials such as EDDHA and EDDHMA, from Akzo-Nobel, the stoichiometry may be 1:1 zinc to ligand or 2:1. The chelating agents EDDHA, EDDHMA are intended to cover all their isomeric forms. Non-limiting examples of chelating agents covered by the term EDDHA include o,o-EDDHA (ethylenediamine-N,N'-di(2-hydroxyphenyl acetic acid), and o,p-EDDHA-ethylenediamine-N-(2-hydroxyphenyl acetic acid)-N'-(4-hydroxyphenyl acetic acid) and examples of the chelating agent EDDHMA include o,o-EDDHMA-ethylenediamine-N,N'-di(2-hydroxy-4-methylphenyl acetic acid), and o,o'-EDDHMA-ethylenediamine-N-(2-hydroxy-4-methylphenyl acetic acid)-N'-(2-hydroxy-6-methylphenyl acetic acid).

c) 2-Pyridinol-N-Oxide Materials

2-Pyridinol-N-oxide materials suitable for use in this invention include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

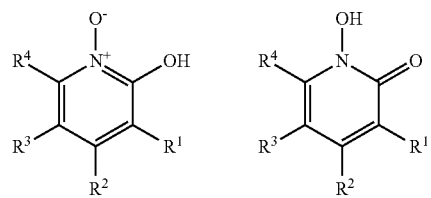

where $R^1$, $R^2$, $R^3$, $R^4$ groups are independently selected from the group consisting of H, Cl, Br, I, F, NO, $NO_2$, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $+N(R^7R^8R^9R^{10})$ and $1/q\ M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide material is a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1. In other aspects, the 2-pyridinol-N-oxide material is a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

In certain aspects, the 2-pyridinol-N-oxide material is the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, $½ Mg^{2+}$, or $½ Ca^{2+}$, substituted ammonium, such as $C_1$-$C_6$ alkanolammnonium, mono-ethanolamine (MEA), triethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

In certain aspects, the 2-pyridinol-N-oxide material is of a substituted or unsubstituted 2-pyridinol-N-oxide material. Salts for use herein include those formed from the polyvalent metals barium, bismuth, strontium, copper, zinc, cadmium, zirconium and mixtures thereof.

In some aspects, the 2-pyridinol-N-oxide material is selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, MO) and/or Aces Pharma (Branford, CT).

In certain aspects, the 2-pyridinol-N-oxide material is a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide material is a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, MO), Princeton Building Blocks (Monmouth Junction, NJ), 3B Scientific Corporation (Libertyville, IL), SynFine Research (Richmond Hill, ON), Ryan Scientific, Inc. (Mt. Pleasant, SC), and/or Aces Pharma (Branford, CT).

In certain aspects, the 2-pyridinol-N-oxide material is a 2-pyridinol-N-oxide material or tautomer thereof according to the formula(s) below:

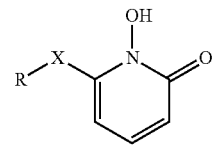

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

In certain aspects, the 2-pyridinol-N-oxide material is a 2-pyridinol-N-oxide material or tautomer thereof according to the formula(s) below:

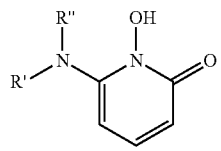

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N- oxide material is 1-Hydroxy-4-methyl-6-(2,4,4-trimethylpentyl)-2-pyridone monoethanolamine salt.

In the present invention, the personal care composition may contain from about 0.1% to about 10% of a substituted or unsubstituted 2-pyridinol N-oxide material; from about 0.1% to about 4% piroctone olamine; from about 0.3% to about 3% of a substituted or unsubstituted 2-pyridinol N-oxide material; from about 0.5% to about 2% of a substituted or unsubstituted 2-pyridinol N-oxide material.

In the present invention, application on the scalp or skin of compositions that comprise an antimicrobial active, which may include an anti-fungal active or an anti-dandruff active, and a chelating agent followed by exposure of the skin or scalp with electromagnetic radiation that corresponds to UV-Visible spectrum at wavelength of 350 nm to 500 nm may provide superior efficacy with an additional benefit of hair growth or re-growth may be stimulated or regulated, or both, or that hair loss may be reduced or inhibited, or that hair may appear thicker or fuller.

Fungal Growth Sensitivity Test

Cells are grown in the medium of choice, generally one requiring respiration. In the case of *Malassezia furfur* that medium is modified Dixon medium (mDixon) (per one liter: 36 g malt extract (Difco 0186-17), 20 g ox bile (provided by American Laboratories, Inc., of Omaha, Nebraska, as Lot No. 03130792), 10 ml Tween 40 (Aldrich 27435-6), 6 g peptone (Difco 0118-17), 2 ml oleic acid (Baker 2114-01), and 2 ml glycerol (Sigma G-7893)). [*Candida* and YPG, *Saccharomyces* and YNB (without amino acids) to which we added 40 µg/ml each of uracil, histidine, and methionine plus 130 µg/ml leucine and 2% ethanol and 0.1% yeast extract.] Conventional medium may also be used for other microbials. Starting cultures are prepared by diluting a fresh overnight culture that is out of log phase 1:100 and incubating with shaking at 31° C. in a 250 mL shake flask (Corning, 431144) with 20 mL medium shaking at 200-250 rpm for about 3 hours to ensure the cells had returned to growth phase. At this time, the test agent is added to the flasks to afford the final concentration for testing. The cells are cultured for 1 hour with the test agent. At this time, the cells typically have an OD at 600 nm in the range of 0.25 to 0.8. Generally, we isolate 2.5 OD*mLs of cells calculated as desired OD*mLs divided by the OD600 of the cells. These media samples are centrifuged (Beckman Coulter Allegra™ 6KR centrifuge) 10 minutes at RT at 3200 rpm to pellet the cells. The supernatant is poured off and the tubes are set upside down on a folded paper towel to drain off the remains of media. Two and one half milliliters of PBS (Gibco, pH 7.4, without magnesium chloride or calcium chloride, 14190-144) is added and the cells resuspended. One mL of cells is transferred to each of two 12-well plates (Falcon, polystyrene, 353043). One plate is stored in the dark and the other is exposed to the light with the plate cover on the plate. A range of 10-15 minute exposure is typically used although optionally, tests have successfully tested longer and shorter times. When the light exposure is completed, the samples are mixed by slowly vortexing or pipetting and 0.65 mL of each sample is transferred to 13 mL of medium for overnight growth at 31° C. with shaking. The following morning, typically 18 hours later, the ODs at 600 nm are determined. Successful materials are those that show at least a 50% reduction in growth after light exposure relative to a dark sample.

Fractional Inhibitor Concentration (FIC)

Fractional Inhibitor Concentration (FIC) is a conventional methodology for evaluating the interaction of two antimicrobial chemicals. It is an effective way to show that using a combination of two treatments results in an effect that is more than what is expected by adding together the effect of the individual treatments, i.e. synergy. In an embodiment of the present invention, FIC is used to determine combinatorial effects of one chemical and exposure to light on *Malassezia* growth and/or viability in an in vitro system.

I. Method Overview:
1. *M. furfur* CBS 7982 cells are exposed to a varying concentrations of an antimicrobial active (e.g. ZPT, Piroctone Olamine) for a specified amount of time (e.g. 2 min to 3 hours).
2. After exposure, the antimicrobial is washed away by centrifugation of the cells and a series of washes
3. Cells are then exposed to light at a wavelength of 409 nm for varying lengths of time
4. Cells are then allowed to grow up overnight (e.g. 17 h) to determine the impact of the treatment on viability and growth of the organism by measuring OD600

II. Data Analysis:
1. Inhibition of growth is determined to be where the OD value obtained is <=50% of the untreated control
2. The lowest concentration value of the antimicrobial agent which inhibits growth is determined
3. Likewise, the shortest light exposure time is determined that gives growth inhibition
4. Finally, the combination of the lowest concentration of the antimicrobial and the shortest light exposure time that provides growth inhibition is determined
5. The FIC value is determined using the calculation below:

$$FIC = \frac{\text{lowest concentration of antimicrobial in combination with light}}{\text{lowest concentration of antimicrobial alone}} + \frac{\text{shortest light time in combination with antimicrobial}}{\text{shortest light time alone}}$$

6. The combinatorial effect of the antimicrobial and light is classified according to the chart below:

| FIC VALUE | Combinatorial Effect |
|---|---|
| <=0.5 | Synergistic |
| >0.5-1.0 | Additive |
| >1.0-<=4.0 | Indifferent |
| >4 | Antagonistic |

Results

*S. cerevisiae* is exposed to light from LED flashlights of the indicated wavelength as well as a painter's light/worklight, commonly found at a hardware store, which provides a broad spectrum of wavelengths of light. Yeast has been pretreated as indicated, prior to light exposure.

TABLE 1 a. Effect of Light and ZPT on *S. cerevisiae* BY4741 in YNB Ethanol, 17 hours growth

| | 17 h growth | | | | |
|---|---|---|---|---|---|
| | Dark | Broad Spectrum | 395 nm | 520 nm | 580 nm |
| No Treatment | 2.443 | 1.982 | 2.2705 | 2.3465 | 2.1845 |
| ZPT, 0.8 ppm | 1.5185 | 0.525 | 0.7205 | 1.418 | 1.332 |
| ZPT, 1.6 ppm | 1.525 | 0.303 | 0.3435 | 1.3615 | 0.9245 |

Table 1 demonstrates that ZPT-treated. *S. cerevisiae* becomes sensitive to a 395 nm flashlight, but not two other wavelengths of light.

*M. furfur* is incubated for twenty minutes with the indicated treatment. A cell pellet is collected after centrifugation so that most of the anti-fungal materials is expected to have been removed. The cell pellet is suspended in PBS and either treated with light (409 nm, 1100 foot candles) for ten minutes or stored in the dark for ten minutes. Samples are then diluted into mDixon with subsequent growth indicated by OD 600 nm.

TABLE 2

| | Dark | Light |
|---|---|---|
| No Treatment | 8.97 | 7.26 |
| ZPT, 4 ppm | 10.14 | 4.86 |
| ZPT, 8 ppm | 9.02 | 3.16 |
| ZPT, 16 ppm | 5.72 | 0.24 |
| ZPT, 24 ppm | 5.54 | 2.41 |
| ZPT, 32 ppm | 2.61 | 1.65 |
| Piroctone Olamine, 8 ppm | 7.82 | 7.35 |
| Piroctone Olamine, 16 ppm | 7.90 | 0.07 |
| Piroctone Olamine, 24 ppm | 7.07 | 0.03 |
| Piroctone Olamine, 32 ppm | 6.76 | 0.02 |
| Piroctone Olamine, 48 ppm | 7.21 | 0.03 |
| Piroctone Olamine, 64 ppm | 7.23 | 0.02 |

Table 2 demonstrates that with ZPT treatment without light exposure, *M. furfur* shows some growth inhibition from treatment in the original flask with ZPT at 16 to 32 ppm. There is little or no effect of light on yeast that had not been previously treated with either ZPT or piroctone olamine. With the addition of light, there is considerable growth inhibition with prior treatment by either ZPT or piroctone olamine.

*M. furfur* is incubated for one hour with the indicated concentrations of Piroctone Olamine then a cell pellet of 4 OD*mL is collected by centrifugation so that most of the anti-fungal material has been removed. The cell pellet is suspended in 4.2 mL PBS and 1 mL samples are distributed to four 12 well plates and treated with light (409 nm, 1200 fc) for 1, 10 or 60 minutes or stored in the dark. Samples are processed as described previously with 600 uL diluted into 13 mL mDixon and 50 uL of the photolyzed cells are diluted into 50 uL of mDixon then three 40 uL+360 uL mDixon dilutions are prepared. They are dosed onto duplicate mDixon agar plates, one set is presented in the Table 3.

TABLE 3

| Culture Dilution | Dark | 1 min. | 10 min. | 60 min |
|---|---|---|---|---|
| 0 ppm Piroctone Olamine | | | | |
| 1:2 | + | + | + | + |
| 1:20 | + | + | + | + |
| 1:200 | +/− | +/− | +/− | +/− |
| 1:2000 | +/− | +/− | +/− | +/− |
| 8 ppm Piroctone Olamine | | | | |
| 1:2 | + | + | + | + |
| 1:20 | + | + | + | + |
| 1:200 | +/− | +/− | +/− | +/− |
| 1:2000 | +/− | +/− | +/− | +/− |
| 16 ppm Piroctone Olamine | | | | |
| 1:2 | + | + | +/− | +/− |
| 1:20 | + | +/− | +/− | +/− |
| 1:200 | +/− | +/− | − | − |
| 1:2000 | +/− | +/− | − | − |
| 32 ppm Piroctone Olamine | | | | |
| 1:2 | + | + | +/− | +/− |
| 1:20 | + | +/− | +/− | +/− |
| 1:200 | +/− | +/− | +/− | − |
| 1:2000 | +/− | +/− | − | − |

Where +=a continuous fungal lawn, +/−=a lawn with breaks allowing the agar to show, −=0 to 5 colonies Table 3 demonstrates an experiment using Piroctone Olamine doses of 0, 8, 16 and 32 ppm with light at 0, 1, 10 and 60 minutes. In this experiment, 8 ppm Piroctone Olamine does not hold *M. furfur* growth down overnight in the original samples, but 16 and 32 ppm do. After the photolysis, 0.6 mL is added to 13 mL fresh mDixon and grown overnight but, in addition, 50 uL is added to 50 uL mDixon then that sample is diluted 3 more times 40 uL=>400 uL and 10 uL of each of the dilutions are plated in duplicate on mDixon agar plates. The plate shows that light has no effect on the control leg with no piroctone olamine and there is no effect with 8 ppm piroctone olamine however, 16 and 32 ppm showed about 10-fold fewer viable cells with 1 minute of light exposure with longer exposures showing >100 fold fewer cells.

Potentiation of Piroctone Olamine by light exposure is also observed in *Candida albicans*. *C. albicans* cells are exposed to varying concentrations of Piroctone Olamine (as indicated on the top row of the table) and then exposed to 409 nm light for 15 min. Cells are then diluted as indicated in the left column, and spot plated. Resulting growth is then scored, as explained above. As can be seen in Table 4, with the 12 and 24 ppm dose of Piroctone Olamine, the addition of light results in complete inhibition of growth. This data suggests that the combination of light and iron chelators is a viable approach in multiple types of yeast and fungi.

TABLE 4

| | NT | 6 ppm | 12 ppm | 24 ppm |
|---|---|---|---|---|
| Dark | | | | |
| 1:2 | + | + | + | + |
| 1:20 | + | + | + | + |
| 1:200 | +/− | +/− | +/− | +/− |
| 1:2000 | +/− | +/− | +/− | +/− |

TABLE 4-continued

|  | NT | 6 ppm | 12 ppm | 24 ppm |
|---|---|---|---|---|
|  | 15 minute 409 nm light | | | |
| 1:2 | + | + | + | + |
| 1:20 | + | + | +/− | +/− |
| 1:200 | +/− | +/− | +/− | +/− |
| 1:2000 | +/− | +/− | − | − |

Dependence of photosensitivity on wavelength. A fresh overnight culture is diluted 100 fold and grown for three hours to an OD of 0.16. *M. furfur* is treated at the indicated dose and cultured another three hours. Cells are harvested by centrifugation, suspended in PBS, and exposed to an LED array at the indicated wavelength. The illumination is for ten minutes with 1200 foot candles. The cultures are then allowed to grow overnight in mDixon. N=1.

TABLE 5

|  | Dark | 409 nm | 520 nm | 595 nm |
|---|---|---|---|---|
| No Treatment | 7.22 | 4.33 | 4.33 | 4.95 |
| ZPT, 6 ppm | 3.31 | 0.354 | 3.37 | 3.75 |
| Piroctone Olamine, 8 ppm | 4.36 | 0.891 | 4.34 | 5.59 |
| Piroctone Olamine, 12 ppm | 2.79 | 0.068 | 3.76 | 4.22 |

Table 5 demonstrates observed photosensitivity with an LED array of 409 nm light, but not with LED arrays of 520 (green) and 595 (yellow) light for both ZPT and Piroctone Olamine The combination of ZPT and light demonstrates a synergistic interaction. *M. furfur* is incubated for three hours with varying concentrations of ZPT. Cell pellets are collected by centrifugation so that most of the anti-fungal material has been removed. The cell pellet is suspended in PBS and 500 uL samples are distributed to four 12 well plates and treated with light (409 nm) for 2, 10 or 60 minutes or stored in the dark. Samples are then diluted into mDixon, and incubated for 16 h with subsequent growth measured by OD 600 nm.

TABLE 6

| ZPT | Light (min) | | | |
|---|---|---|---|---|
| (ppm) | 0 | 2 | 10 | 60 |
| 0 | 12.69 | 10.39 | 13.06 | 6.82 |
| 1.25 | 7.76 | 7.24 | 6.24 | 1.96 |
| 2.5 | 7.12 | 3.35 | 0.31 | 0.03 |
| 5 | 6.21 | 5.30 | 3.72 | 0.87 |
| 10 | 4.85 | 4.91 | 4.06 | 0.83 |
| 20 | 0.51 | 0.58 | 0.64 | 0.37 |

As shown in the data in Table 6, the lowest concentration of ZPT to give growth inhibition is 10 ppm. The shortest length of time of light exposure to give growth inhibition is >60 min. The lowest concentration and shortest light exposure time when applied in combination to give growth inhibition is 2.5 ppm and 2 min, respectively. Using the formula indicated above, a FIC value of 0.28 is calculated. A FIC value of <=0.5 indicates synergy, and therefore the combination of ZPT and light is a synergistic one.

The combination of Piroctone Olamine and light also demonstrates a synergistic interaction. *M. furfur* is incubated for one hour with varying concentrations of Piroctone Olamine. Cell pellets are collected by centrifugation so that most of the anti-fungal material has been removed. The cell pellet is suspended in PBS and 500 uL samples are distributed to four 12 well plates and treated with light (409 nm) for 1, 10 or 60 minutes or stored in the dark. Samples are then diluted into mDixon, and incubated for 16 h with subsequent growth measured by OD 600 nm.

TABLE 7

| Piroctone Olamine | Light (min) | | | |
|---|---|---|---|---|
| (ppm) | 0 | 1 | 10 | 60 |
| 0 | 3.6 | 3.6 | 4.1 | 2.2 |
| 4 | 3.6 | 4.1 | 3.9 | 3.7 |
| 8 | 3.9 | 0.1 | 0.0 | 0.0 |
| 16 | 2.6 | 0.1 | 0.0 | 0.0 |
| 32 | 2.1 | 0.2 | 0.0 | 0.0 |
| 64 | 1.3 | 0.1 | 0.0 | 0.0 |

As shown in the data in Table 7, the lowest concentration of Piroctone Olamine to give growth inhibition is 64 ppm. The shortest length of time of light exposure to give growth inhibition is >60 min. The lowest concentration and shortest light exposure time when applied in combination to give growth inhibition is 8 ppm and 1 min, respectively. Using the formula indicated above, a FIC value of 0.14 is calculated. A FIC value of <=0.5 indicates synergy, and therefore the combination of Piroctone Olamine and light is a synergistic one.

The combination of Hinokitiol and light also demonstrates a synergistic interaction. *M. furfur* is incubated for one hour with varying concentrations of Hinokitiol. Cell pellets are collected by centrifugation so that most of the anti-fungal material has been removed. The cell pellet is suspended in PBS and 500 uL samples are distributed to four 12 well plates and treated with light (409 nm) for 1, 10 or 60 minutes or stored in the dark. Samples are then diluted into mDixon, and incubated for 27 h with subsequent growth measured by OD 600 nm.

TABLE 8

| Hinokitiol | Light (min) | | | |
|---|---|---|---|---|
| (ppm) | 0 | 1 | 10 | 60 |
| 0 | 8.8 | 8.6 | 8.7 | 8.6 |
| 3 | 8.3 | 7.9 | 4.6 | 4.5 |
| 6 | 8.5 | 1.8 | 0.3 | 0.4 |
| 12 | 8.6 | 2.3 | 0.2 | 0.3 |
| 24 | 6.1 | 0.6 | 0.2 | 0.2 |
| 48 | 5.7 | 0.2 | 0.1 | 0.1 |
| 96 | 5.9 | 0.3 | 0.0 | 0.0 |

As shown in the data in Table 8, the lowest concentration of Hinokitiol to give growth inhibition is >96 ppm. The shortest length of time of light exposure to give growth inhibition is >60 min. The lowest concentration and shortest light exposure time when applied in combination to give growth inhibition is 6 ppm and 1 min, respectively. Using the formula indicated above, a FIC value of 0.08 is calculated. A FIC value of <=0.5 indicates synergy, and therefore the combination of Hinokitiol and light is a synergistic one.

The combination of HPNO (2-Hydroxypyridine N-oxide) and light also demonstrates a synergistic interaction. *M. furfur* is incubated for one hour with varying concentrations of HPNO. Cell pellets are collected by centrifugation so that most of the anti-fungal material has been removed. The cell pellet is suspended in PBS and 500 uL samples are distributed to four 12 well plates and treated with light (409 nm) for 1, 10 or 60 minutes or stored in the dark. Samples are then diluted into mDixon, and incubated for 23 h with subsequent growth measured by OD 600 nm.

TABLE 9

| HPNO (ppm) | Light (min) | | | |
|---|---|---|---|---|
| | 0 | 1 | 10 | 60 |
| 0 | 7.7 | 8.2 | 6.9 | 6.5 |
| 15 | 9.0 | 8.9 | 7.2 | 7.5 |
| 30 | 8.0 | 7.3 | 4.7 | 5.1 |
| 60 | 7.5 | 3.9 | 3.3 | 2.1 |
| 120 | 6.7 | 2.1 | 0.2 | 0.1 |
| 240 | 4.6 | 0.2 | 0.0 | 0.0 |
| 480 | 4.7 | 0.1 | 0.0 | 0.0 |

As shown in the data in Table 9, the lowest concentration of HPNO to give growth inhibition is >480 ppm. The shortest length of time of light exposure to give growth inhibition is >60 min. The lowest concentration and shortest light exposure time when applied in combination to give growth inhibition is 60 ppm and 1 min, respectively. Using the formula indicated above, a FIC value of 0.14 is calculated. A FIC value of <=0.5 indicates synergy, and therefore the combination of HPNO and light is a synergistic one.

Protoporphyrin IX levels increase due to exposure to iron chelators. The molecular basis for increased susceptibility to light at ~400 nm after exposure to various iron chelators is hypothesized to be due to increased levels of protoporphyrin IX (PPIX). As shown in Table 10, treatment of *M. furfur* cells with increasing concentrations of either Piroctone Olamine or ZPT results in increased levels of PPIX, as measured by HPLC. PPIX absorb light in the 400 nm range, and when light is absorbed, PPIX transitions to an excited triplet state that can react with triplet oxygen to produce singlet oxygen or the excited porphyrin can generate ROS through single electron processes. These reactive species result in a loss of cell viability. This underscores the importance of the wavelength of light that is important to see the synergistic benefit of light and chelator.

TABLE 10

| | Piroctone Olamine (ppm) | | | | | ZPT (ppm) | | | |
|---|---|---|---|---|---|---|---|---|---|
| | 0 | 6 | 8 | 16 | 32 | 0 | 2.5 | 5 | 10 |
| Total PPIX (ng) | 3.1 | 2.6 | 13.9 | 20.7 | 16.5 | 0.13 | 0.37 | 0.47 | 0.27 |

TABLE 11

| | OD600 | | PPIX |
|---|---|---|---|
| | Dark | Light | (ng) |
| Untreated | 8.07 | 6.15 | 4.4 |
| SeSx (0.4 ppm) | 3.31 | 2.27 | 2.6 |
| SeSx (0.8 ppm) | 1.51 | 1.44 | 1.2 |
| Sulfur (8 ppm) | 4.52 | 3.62 | 1.6 |

| | OD600 | | |
|---|---|---|---|
| | Dark | Light | PPIX |
| Untreated | 12.4 | 12.4 | 4.2 |
| Climbazole (1 ppm) | 11.9 | 10.2 | 4.5 |
| Terbinafine (0.5 ppm) | 12.5 | 10.6 | 6.7 |

Not all antifungals demonstrate synergy with light exposure. *M. furfur* cells are exposed to other antifungals that are not considered chelators (i.e. selenium sulfide (SeSx), Sulfur, Climbazole, and Terbinafine). After treatment, cells are then exposed to light, or not exposed to light. Both OD are measured to measure growth and PPIX levels are measured. As seen by the OD values in Table 11, the addition of light to treatment with these non-chelator antifungals does not increase their efficacy. This can be partly explained by the fact that these antifungals do not work by a mechanism that increase PPIX levels, as is seen in Table 11 that PPIX levels do not change upon treatment with these antifungals.

In the present invention a method of treating skin and scalp may be achieved by the following steps:
 a. Applying on the scalp or skin a composition comprising a scalp care active agent selected from the group containing pyrithione metal salt, piroctone olamine, one and more iron chelating agent having an A log P value of greater than or equal to 0.4. and mixtures therein;
 b. Exposing the scalp and skin to electromagnetic radiation having wavelength from about 350 nm to about 500 nm, or from 380 nm to about 450 nm; or from about 400 nm to about 425 nm and power from about 0.1 mWatts/cm$^2$ to about 1000 mWatts/cm$^2$; or from about 0.3 mWatts/cm$^2$ to about 200 mWatts/cm$^2$; or from about 0.5 mWatts/cm$^2$ to about 75 mWatts/cm$^2$ and for a time period from about 2 seconds to about 5 minutes; or from about 10 seconds to about 2 minutes, or from about 10 seconds to 10 minutes; or from about 2 seconds to about 15 minutes; or from about 2 seconds to about 30 minutes.
  wherein this method results in a reduction of fungal growth as measured by the Fungal Growth Sensitivity Test of at least 50% compared to the dark sample.

Non-limiting examples of sources of electromagnetic radiation to apply to the scalp or skin may be a hat, cap, comb, brush or wand.

Detersive Surfactant

The present invention may be present in the form of a shampoo, conditioner, or leave on treatment. The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Further, zwitterionics such as betaines may be selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Second Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Additional Components

The shampoo composition, conditioner compositions, and/or leave-on treatments described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care compositions may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Benefit Agents

The hair care composition may further comprise one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, and treatment products; and any other form that may be applied to hair.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating skin and scalp comprising
   a. Applying on the scalp or skin a composition comprising a scalp care active selected from the group consisting of 2-Pyridinol-N-oxide, a pyrithione or a polyvalent metal salt of pyrithione, one or more iron chelator having an A log P value of greater than or equal to 0.4 and mixtures therein; wherein the scalp care active is present from about 0.01% to about 5%; wherein the one or more iron chelator is selected from the group consisting of catechols and phenols;
   b. Exposing the scalp and skin to electromagnetic radiation having wavelength from about 380 nm to about 450 nm and power from about about 0.1 mWatts/cm$^2$ to about 1000 mWatts/cm$^2$ and for a time period from about 10 seconds to about 2 minutes;
 wherein an antimicrobial treatment results in reduction of fungal growth as measured by a Fungal Growth Sensitivity Test of at least 50% compared to a dark sample.

2. The method of claim 1, wherein the method further comprises rinsing of the composition with water from the scalp or skin.

3. The method according to claim 1 wherein the method comprises leaving the composition on the scalp of skin.

4. The method according to claim 1, wherein the composition comprises an aqueous carrier.

5. The method according to claim 1, wherein the electromagnetic radiation has a wavelength from about 400 nm to about 425 nm.

6. The method according to claim 1, wherein the power is from about 0.3 mWatts/cm$^2$ to about 200 mWatts/cm$^2$.

7. The method according to claim 1, wherein the power is from 0.5 mWatts/cm$^2$ to about 75 mWatts/cm$^2$.

* * * * *